United States Patent [19]

Wenzelburger et al.

[11] 4,079,136

[45] Mar. 14, 1978

[54] IMIDAZOLYLACETIC ACID AMIDES, THEIR PRODUCTION, ANTIMYCOTIC COMPOSITIONS COMPRISING SAID COMPOUNDS AND THEIR USE AS ANTIMYCOTIC AGENTS

[75] Inventors: Jürgen Wenzelburger; Karl Heinz Büchel; Manfred Plempel; Werner Meiser, all of Wuppertal, Germany

[73] Assignee: Bayer Aktiengesellschaft, Germany

[21] Appl. No.: 710,583

[22] Filed: Aug. 2, 1976

Related U.S. Application Data

[62] Division of Ser. No. 651,419, Jan. 22, 1976, Pat. No. 4,032,636, which is a division of Ser. No. 594,195, July 9, 1975, Pat. No. 4,024,270, which is a division of Ser. No. 400,263, Sept. 24, 1973, Pat. No. 3,950,354.

[30] Foreign Application Priority Data

Sep. 26, 1972 Germany .......................... 2247187

[51] Int. Cl.$^2$ .................. A61K 31/495; A61K 31/54; A61K 31/415
[52] U.S. Cl. ................................. 424/250; 424/246; 424/273 R
[58] Field of Search ........................................ 424/250

[56] References Cited

U.S. PATENT DOCUMENTS 3,732,242  5/1975  Buchel et al. ........................ 260/309

OTHER PUBLICATIONS

Chemical Abstracts 74:53800v (1971).
Chemical Abstracts 77:5468h (1972).
Chemical Abstracts 76:59636j (1972).

*Primary Examiner*—Jerome D. Goldberg
*Attorney, Agent, or Firm*—Jacobs & Jacobs

[57] ABSTRACT

The invention relates to imidazolylcarboxylic acid amide antimycotic compositions and their use.

26 Claims, No Drawings

IMIDAZOLYLACETIC ACID AMIDES, THEIR PRODUCTION, ANTIMYCOTIC COMPOSITIONS COMPRISING SAID COMPOUNDS AND THEIR USE AS ANTIMYCOTIC AGENTS

This is a division of Ser. No. 651,419, filed Jan. 22, 1976, now U.S. Pat. No. 4,032,636, which is a divisional of Ser. No. 594,195, filed July 9, 1975, now U.S. Pat. No. 4,024,270, which is a division of Ser. No. 400,263, filed Sept. 24, 1973, which issued as U.S. Pat. No. 3,950,354, on Apr. 13, 1976.

The present invention relates to imidazolylcarboxylic acid amides, their production, antimycotic compositions embodying said compounds of the active ingredient, and to their use as antimycotic agents.

More particularly, the present invention is concerned with imidazolylacetic acid amides of the formula:

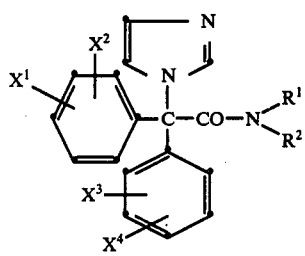

(I)

and pharmaceutically acceptable nontoxic salts thereof wherein
either
R$^1$ is phenyl or cycloalkyl, unsubstituted or substituted by one or more substituents; and
R$^2$ is hydrogen;
or
R$^1$ and R$^2$, together with the nitrogen atom to which they are attached, form a saturated 5 to 7-membered heterocyclic ring which ring may contain an —SO$_2$— or —NY— moiety wherein Y is alkoxycarbonyl, dialkylaminocarbonyl, or phenyl or diphenylmethyl, unsubstituted or substituted by one or more substituents and wherein said 5 to 7-membered heterocyclic ring is itself either or otherwise unsubstituted or substituted by one or more substituents; and
X$^1$, X$^2$, X$^3$ and X$^4$ are the same or different and are each hydrogen or halogen.

The imidazolylacetic acid amides of formula (I) are produced by:
(a) reacting a halodiphenylacetic acid amide of the formula:

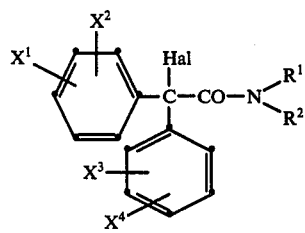

(II)

wherein
R$^1$, R$^2$, X$^1$, X$^2$, X$^3$ and X$^4$ are as above defined, and
Hal is halogen,
with imidazole; or (b) reacting a halodiphenylacetic acid halide of the formula:

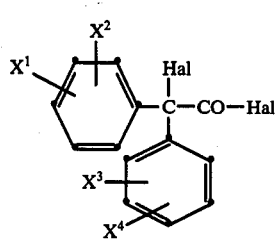

(III)

wherein
X$^1$, X$^2$, X$^3$ and X$^4$ are as above defined, and
Hal is halogen
with imidazole to produce an imidazolide of the formula:

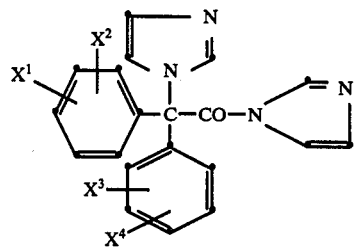

(IV)

wherein
X$^1$, X$^2$, X$^3$ and X$^4$ are as above defined which in turn is transaminated by reaction with an amine of the general formula:

NHR$^1$R$^2$ (V)

wherein
R$^1$ and R$^2$ are as above defined.

The above two processes are hereinafter referred to as Process Variants (a) and (b).

When R$^1$ is cycloalkyl, it is preferably a cycloalkyl moiety of 5 to 7 carbon atoms and especially 6 carbon atoms. Cyclopentyl, cyclohexyl and cycloheptyl are examples.

When the phenyl or cycloalkyl moieties of R$^1$ are substituted, they are preferably substituted by 1 to 3 of the same or different substituents, but especially one substituent. Preferred substituents are alkyl of 1 to 4 carbon atoms, especially alkyl of 1 to 3 carbon atoms, i.e., methyl, ethyl, n- and i-propyl, halogen (preferably chlorine, fluorine and bromine, especially chlorine), haloalkyl of 1 or 2 carbon atoms and 2 to 5 halogen atoms (preferably chlorine or fluorine and especially fluorine, the trifluoromethyl moiety being preferred), and nitro.

When R$^1$ and R$^2$, together with the amide nitrogen atom to which they are attached, form a 5 to 7-membered heterocyclic ring, said ring may contain a —SO$_2$— or —NY— moiety. The preferred heterocyclic rings are those containing 5 or 6 ring members and especially 6 ring members. When —SO$_2$— or —NY— is contained in the 6-membered heterocyclic ring, it is preferably in the p-position to the amide nitrogen. When the ring contains a —NY— moiety in the ring and Y is alkoxycarbonyl, it is preferred that the alkoxycarbonyl be of 2 to 4 carbon atoms and especially 2 or 3 carbon atoms, i.e., methoxycarbonyl, ethoxycarbonyl and n- and i-propoxycarbonyl. When Y is a dialkylaminocarbonyl, each alkyl moiety may be the same or different and be of 1 to 4 carbon atoms and especially 1 or 2 carbon atoms such as dimethyl, diethyl, methylethyl, methyl-n-propyl or ethylisobutyl. The phenyl and diphenylmethyl moieties of Y are either unsubstituted or substituted by preferably 1 to 3 of the same or different substituents selected from the group consisting of alkyl of 1 to 4 carbon atoms, especially alkyl of 1 to 3 carbon atoms, i.e., methyl, ethyl, n- and i-propyl, halogen, preferably chlorine, fluorine or bromine and especially chlorine, haloalkyl of 1 or 2 carbon atoms and 2 to 5 halogen atoms, preferably chlorine and fluorine and especially fluorine, for example trifluoromethyl, and nitro. When said 5 to 7 membered heterocyclic ring is substituted, it is substituted by one or more of the same or different substituents, and preferably one substituent selected from the group consisting of alkyl of 1 to 4 carbon atoms, i.e., methyl, ethyl, n- and i-propyl, and n-, i- and t-butyl, especially alkyl of 1 or 2 carbon atoms, or phenyl unsubstituted or substituted by a member selected from the group consisting of alkyl of 1 to 4 carbon atoms, especially alkyl of 1 to 3 carbon atoms, i.e., methyl, ethyl, n- and i-propyl, halogen preferably chlorine, fluorine or bromine, especially chlorine, haloalkyl of 1 or 2 carbon atoms and 2 to 5 halogen atoms, preferably chlorine and fluorine, and especially fluorine, for example, trifluoromethyl and nitro.

$X^1$, $X^2$, $X^3$ and $X^4$ are the same or different hydrogen or halogen, for example, fluorine, chlorine, bromine or iodine and preferably fluorine, chlorine and bromine, especially chlorine.

Hal in formulas II and III is preferably chlorine or bromine, and especially chlorine.

According to one embodiment of the present invention, either $R^1$ is phenyl or cycloalkyl of 5 to 7 carbon atoms, unsubstituted or substituted by 1 to 3 substituents selected from the group consisting of alkyl of 1 to 4 carbon atoms, halogen, haloalkyl of 1 or 2 carbon atoms and 2 to 5 halogen atoms and nitro, and
$R^2$ is hydrogen, or
$R^1$ and $R^2$, together with the nitrogen atom to which they are attached, form a saturated 5 to 7-membered heterocyclic ring containing a —$SO_2$— or —NY— moiety wherein Y is alkoxycarbonyl of 2 to 4 carbon atoms, dialkylaminocarbonyl of 1 to 4 carbon atoms in each alkyl moiety, phenyl or diphenylmethyl, unsubstituted or substituted by 1 to 3 substituents selected from the group consisting of alkyl of 1 to 4 carbon atoms, halogen, haloalkyl of 1 or 2 carbon atoms and 2 to 5 halogen atoms, and nitro, said heterocyclic ring being otherwise unsubstituted or substituted by alkyl of 1 to 4 carbon atoms or phenyl unsubstituted or substituted by 1 to 3 substituents selected from the group consisting of alkyl of 1 to 4 carbon atoms, halogen, haloalkyl of 1 or 2 carbon atoms and 2 to 5 halogen atoms, and nitro, and
$X^1$, $X^2$, $X^3$ and $X^4$ are the same or different and are each hydrogen or halogen.

According to another embodiment of the present invention, either
$R^1$ is phenyl or cyclohexyl, unsubstituted or substituted by 1 or 2 substituents selected from the group consisting of alkyl of 1 to 3 carbon atoms, chlorine, fluorine, bromine, trifluoromethyl and nitro, and
$R^2$ is hydrogen, or
$R^1$ and $R^2$, together with the nitrogen atom to which they are attached, form a 6-membered heterocyclic ring containing a —$SO_2$— or —NY— moiety wherein Y is phenyl, diphenylmethyl, methoxycarbonyl, ethoxycarbonyl, dimethylaminocarbonyl or diethylaminocarbonyl, said heterocyclic ring containing a —$SO_2$— moiety being either unsubstituted or substituted by methyl, ethyl or phenyl, and either
$X^1$, $X^2$, $X^3$ and $X^4$ are each hydrogen, or
$X^1$ and $X^3$ are each halogen and
$X^2$ and $X^4$ are each hydrogen.

According to another embodiment of the present invention, either
$R^1$ is cyclohexyl, or phenyl which phenyl is either unsubstituted or substituted by 1 or 2 substituents selected from the group consisting of alkyl of 1 to 3 carbon atoms, chlorine, fluorine, bromine and trifluoromethyl, and
$R^2$ is hydrogen, or
$R^1$ and $R^2$, together with the nitrogen atom to which they are attached, form a 6-membered heterocyclic ring containing a —$SO_2$— or —NY— moiety wherein Y is phenyl, diphenylmethyl, methoxycarbonyl, ethoxycarbonyl, dimethylaminocarbonyl or diethylaminocarbonyl, said heterocyclic ring containing a —$SO_2$— moiety being either unsubstituted or substituted by methyl, ethyl or phenyl, and
$X^1$, $X^2$, $X^3$ and $X^4$ are each hydrogen, or
$X^1$ and $X^3$ are chlorine and
$X^2$ and $X^4$ are hydrogen.

According to another embodiment of the present invention, either
$R^1$ is cyclohexyl or phenyl, unsubstituted or substituted by 1 or 2 substituents selected from the group consisting of chlorine, methyl and trifluoromethyl; and
$R^2$ is hydrogen; or
$R^1$ and $R^2$, together with the nitrogen atom to which they are attached, form a 6-membered heterocyclic ring selected from the group consisting of

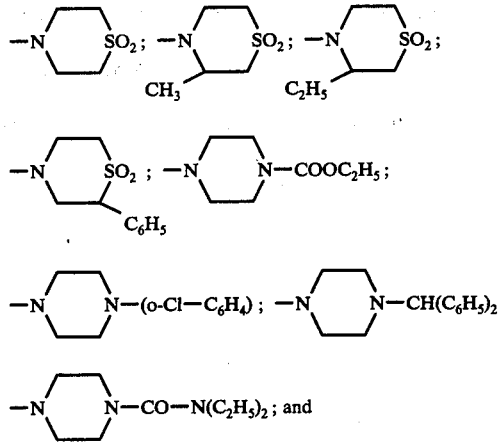

either $X^1$, $X^2$, $X^3$ and $X^4$ are each hydrogen, or
$X^1$ and $X^3$ are chlorine and
$X^2$ and $X^4$ are hydrogen.

According to a further embodiment of the present invention, either $R^1$ cyclohexyl, chlorophenyl, tolyl, trifluoromethylphenyl, dichlorophenyl or chloromethylphenyl, and $R^2$ is hydrogen, or $R^1$ and $R^2$, together with the nitrogen atom to which they are attached, form a 6-membered heterocyclic ring of the formula:

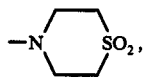

unsubstituted or substituted by methyl, ethyl or phenyl, or

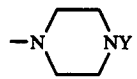

wherein Y is $COOC_2H_5$, chlorophenyl, $CO-N(C_2H_5)_2$ or diphenylmethyl, and $X^1$, $X^2$, $X^3$ and $X^4$ are each hydrogen, or
$X^1$ and $X^3$ are chlorine and
$X^2$ and $X^4$ are hydrogen.

If for example [ω-(4,4'-dichlorodiphenyl)-ω-chloromethylcarbonyl-(4)]-1,4-thiazine dioxide and imidazole are used as the starting compounds, the course of the reaction can be represented by the following equation (Process Variant (a)):

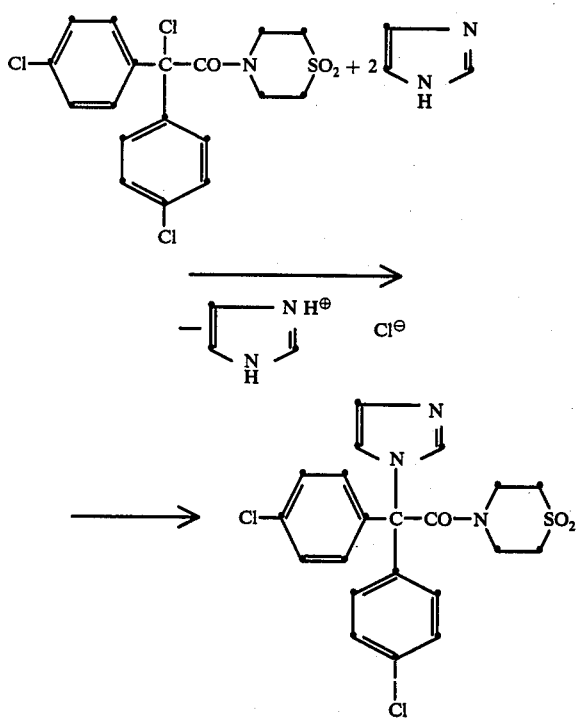

If for example diphenylchloroacetic acid chloride, imidazole and o-methylaniline are used as starting compounds, the course of the reaction can be represented by the following equation (Process Variant (b)):

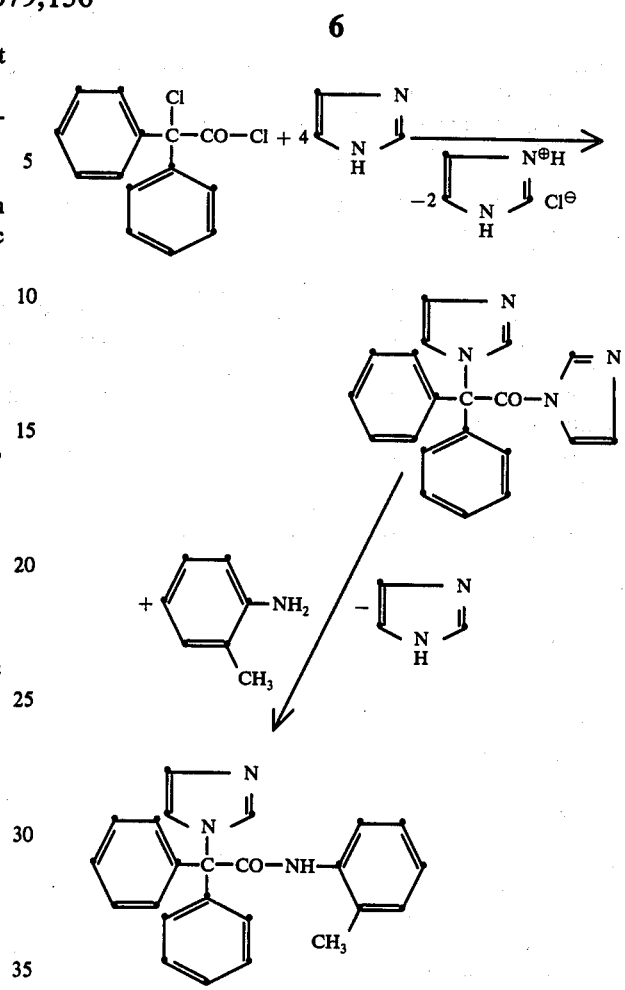

The halodiphenylacetic acid amides used as starting compounds of the formula II are not per se known but can be produced according to procedures per se known, for example, by reacting halodiphenylacetic acid halides of the formula III (some of which are known and can be produced by known methods) with amides of the formula V according to procedures described in Ber. 41, page 3593 (1908). Representative halodiphenylacetic acid amides of formula II include:

ω,ω-diphenyl-ω-chloro-acetic acid p-chloroanilide;
ω,ω-diphenyl-ω-chloro-acetic acid m-trifluoromethylanilide;
ω,ω-diphenyl-ω-chloro-acetic acid 2-methyl-4-chloroanilide;
ω,ω-diphenyl-ω-chloro-acetic acid 2,4-dichloro-anilide;
ω,ω-diphenyl-ω-chloro-acetic acid cyclohexylamide;
ω,ω-di-(4-chlorophenyl)-ω-chloroacetic acid 2-methylanilide;
ω,ω-di-(4-chlorphenyl)-ω-chloro-acetic acid 2,5-dichloroanilide;
[ω,ω-diphenyl-ω-chloro-methylcarbonyl-(4)]-1,4-thiazine dioxide;
3-methyl-4-[ω,ω-di-(4-chlorophenyl)-ω-chloro-methylcarbonyl]-1,4-thiazine dioxide;
3-ethyl-4-[ω,ω-di-(4-chlorophenyl)-ω-chloro-methylcarbonyl]-1,4-thiazine dioxide;
[ω-phenyl-ω-4-chlorophenyl-ω-chloro-methylcarbonyl-(4)-3-phenyl]-1,4-thiazine dioxide;
1-o-chlorophenyl-4-[ω,ω-diphenyl-ω-chloro-methylcarbonyl]-piperazine;

1-diethylaminocarbonyl-4-[ω,ω-diphenyl-ω-chloro-methylcarbonyl]-piperazine and
1-diphenylmethyl-4-[ω,ω-di-(4-chloro-phenyl)-ω-chloromethylcarbonyl]-piperazine.

Representative halodiphenylacetic acid halides of the formula III include:

ω,ω-diphenyl-ω-chloro-acetic acid chloride;
ω,ω-di-(4-chlorophenyl)-ω-chloro-acetic acid chloride;
ω-phenyl-ω-(2-chlorophenyl)-ω-chloro-acetic acid chloride;
ω-phenyl-ω-(3-chlorophenyl)-ω-chloro-acetic acid chloride; and
ω-phenyl-ω-(4-chlorophenyl)-ω-chloro-acetic acid chloride.

Representative amines of the formula V include:

aniline;
o-methylaniline;
o- and p-dichloroaniline;
p-chloroaniline;
m-trifluoroaniline;
p-methylaniline;
p-chloro-m-methylaniline;
p-fluoroaniline;
p-bromoaniline;
o-ethylaniline;
p-nitroaniline;
o-nitroaniline;
p-nitro-o-methylaniline;
cyclohexylamine;
cyclopentylamine and
cycloheptylamine.

The pharmaceutically acceptable nontoxic salts of the compound of the present invention include salts formed by the reaction between the imidazolylacetic acid amide as the free base and hydrohalic acids, such as hydrochloric and hydrobromic acids, especially hydrochloric acid, phosphoric acid, nitric acid, monofunctional and bifunctional carboxylic acids and hydroxycarboxylic acids, for example, acetic acid, maleic acid, succinic acid, fumaric acid, tartaric acid, citric acid, salicylic acid, sorbic acid and lactic acid, and 1,5-naphthalenedisulphonic acid. Hydrochloric acid is especially preferred.

The preferred salts are therefore the hydrohalides, for example, the hydrochloride and hydrobromide, especially the hydrochloride, the phosphate, nitrate, monofunctional and bifunctional carboxylates and hydroxycarboxylates, for example, the acetate, maleate, succinate, fumarate, tartrate, citrate, salicylate, sorbate and lactate, and 1,5-naphthalenedisulphonate. The hydrochloride is especially preferred.

The reaction of the halodiphenylacetic acid and imidazole in Process Variant (a) can be carried out in a diluent which is inert towards the reactants and products. Such diluents include all inert polar organic solvents. Preferred diluents are chlorinated hydrocarbons (especially aromatic chlorinated hydrocarbons, such as chlorobenzene); ketones (especially lower alkyl ketones, such as acetone and diethyl ketone); nitriles (especially those having up to 6 carbon atoms, such as acetonitrile); amides (especially lower dialkylformamides, such as dimethylformamide); and sulphoxides (especially lower dialkylsulphoxides, such as dimethylsulphoxide).

As acid-binding agents, it is possible to use, in Process Variant (a), all the usual acid-binding agents. These include organic and inorganic bases (preferably alkali metal hydroxides, such as sodium hydroxide and potassium hydroxide) and tertiary organic bases (such as trialkylamines, for example triethylamine). In Process Variant (a) according to the invention, we prefer particularly to use an excess of imidazole instead of a separate acid-binding agent.

In the Process Variant (a), the reaction temperatures can be varied over a substantial range. In general, the reaction is carried out at between 50° C and 150° C, preferably between 80° C and 120° C.

The reaction in Process Variant (a) can be carried out under normal pressure but also under elevated pressure. The reaction is preferably carried out under normal pressure.

In carrying out the process according to the invention Process Variant (a), 1 to 5 (preferably 1 to 2) mols of imidazole and additionally 1 to 5 (preferably 1 to 2) equivalents of the acid-binding agent (for example imidazole or triethylamine) are generally employed per 1 mol of the imidazolylcarboxylic acid amides of formula II.

As an example, for the isolation of the free amides of the formula I according to the present invention carried out according to known methods, the solvent is distilled from the reaction mixture, the residue is digested with ice water and the undissolved solid is filtered off and purified by recrystallization. Thereafter any desired salts can be produced by generally customary methods, for example by dissolving the free amide of the formula I in an organic solvent and adding the requisite amount of acid.

The solvents already mentioned in connection with Process Variant (a) can also be used as diluents in the reaction, according to the invention, of the halodiphenylacetic acid halides of the formula III with imidazole in Process Variant (b).

The acid-binding agent used in the first reaction step in Process Variant (b) (reaction of halodiphenylacetic acid halides of the general formula III with imidazole) is preferably an excess of imidazole, appropriately about 4 to 10, preferably 4 to 5, mols of imidazole per 1 mol of starting compound of the formula III.

In the reaction of the compounds of the formula III with imidazole (Process Variant (b)), the reaction temperatures can be varied within a substantial range. In general, the reaction is carried out at between 50° C and 100° C, preferably between 50° C and 100° C.

The imidazolides of the formula IV which are produced in the first reaction step are preferably reacted further without intermediate isolation. However, a prior isolation is possible within the scope of the invention.

In the second reaction step of Process Variant (b) (reaction of the imidazolide of the formula IV with the amine of the formula V) the reaction temperatures can be varied within a substantial range. In general, the reaction is carried out between 50° C and 150° C, preferably between 80° C and 150° C.

In carrying out the second reaction step in Process Variant (b), 1 to 5, more preferably 1 to 2, mols of amine of the formula V are preferably used per 1 mole of imidazolide of the formula IV. Using higher or lower than stoichiometric ratios does not adversely influence the outcome of the reaction.

The working up and isolation of the imidazolylcarboxylic acid amides of the formula I can be carried out according to customary methods, for example as described in connection with Process Variant (a). Thereafter, the salts can be produced according to customary methods, for example as described above.

The following compounds are representative of the imidazolylacetic acid amides of the present invention:

4-[ω,ω-di-(chlorophenyl)-ω-imidazolyl-(1)-methylcarbonyl]-1,4-thiazine dioxide;
ω)ω-diphenyl-ω-imidazolyl-(1)-acetic acid 3-trifluoromethylanilide;
ω,ω-diphenyl-ω-imidazolyl-(1)-acetic acid 2-methyl-4-chloro-anilide;
ω,ω-diphenyl-ω-imidazolyl-(1)-acetic acid 2,4-dichloroanilide;
ω,ω-diphenyl-ω-imidazolyl-(1)-acetic acid cyclohexylamide;
4-[ω,ω-di-(4-chlorophenyl)-ω-imidazolyl-(1)-methylcarbonyl]-3-phenyl-1,4-thiazine dioxide;
4-[ω,ω-diphenyl-ω-imidazolyl-(1)-methylcarbonyl]-1-ethoxycarbonyl-piperazine and
4-[ω,ω-diphenyl-ω-imidazolyl-(1)-methylcarbonyl]-1-o-chlorophenyl-piperazine.

The imidazolylacetic acid amides and the salts of the present invention exhibit strong antimycotic activity. They exhibit a broad spectrum of antimycotic activity especially against dermatophytes and blastomycetes, as well as biphase fungi, for example against species of Candida such as *Candida albicans,* species of Epidermophyton such as *Epidermophyton floccosum,* species of *Aspergillus* such as *Aspergillus niger,* species of Trichophyton such as *Trichophyton mentagrophytes,* species of Microsporon such as *Microsporon felineum,* and species of Penicillium such as *Penicillium commune.*

The compounds of the present invention are deemed to be useful in the treatment of dermatomycoses and systemic mycoses in humans caused by *Trichophyton mentagrophytes* and other species of Trichophyton, species of *Microsporon, Epidermophyton floccosum,* blastomycetes and biphase fungi as well as moulds.

The compounds of the present invention are useful in veterinary medicine and the treatment of dermatomycoses and systemic mycoses, especially those caused by the above mentioned pathogens.

The present invention also includes pharmaceutical compositions comprising an imidazolylacetic acid amide of the present invention in combination with a pharmaceutically acceptable nontoxic, inert diluent or carrier.

The pharmaceutical compositions of the present invention contain a major or minor amount e.g. 99.5 to 0.1%, preferably 95 to 0.5% of at least one imidazolylacetic acid amide as above defined in combination with a pharmaceutically acceptable nontoxic, inert diluent or carrier, the carrier comprising one or more solid, semisolid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 30 to 250, and preferably 50 to 200, mg/kg of body weight per day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and-/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound.

Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose is 1.5 to 22.5 g, preferably 2.5 to 18.0 g, of active agent.

While the compounds of the present invention are suitable for oral, parenteral (for example intramuscular, intraperitoneal and intravenous administration), rectal or topical application, oral administration and topical application are particularly preferred.

The preferred pharmaceutical compositions are therefore those which are suitable for oral or topical administration, such as tablets, pills, granules, lotions and ointments.

The following in vitro and in vivo experimental data illustrate the antimycotic activity of the compounds of the present invention.

Determination of the anti-mycotic spectrum of action in vitro, by the series dilution test.

Description of the experiments

The nutrient substrates used were Sabouraud's milieu d'epreuve for dermatophytes and moulds, and meat broth-glucose bouillon for blastomycetes and biphase fungi.

The incubation temperature was 28° C and the incubation time was 24 to 96 hours.

The experiment results are summarized in Table A.

Table A

| Compound from Example No. | inhibitory concentration in γ/ml of nutrient medium | | | | | | | |
|---|---|---|---|---|---|---|---|---|
| | Trichophyton mentagrophytes | | Candida albicans | | Penicillium commune | Aspergillus niger | | Microsporon felineum |
| | n.s. | w.s. | n.s. | w.s. | | n.s. | w.s. | |
| 13 | 10 | 40 | >100 | — | >100 | 1* | 100* | 100 |
| 4 | 64 | 64 | >64 | >64 | >64 | — | — | — |
| 2 | 100 | — | >100 | — | >100 | — | — | — |
| 12 | 64+ | — | 64+ | >64 | >64 | — | — | — |
| 7 | 32* | >64 | 4* | 8 | >64 | — | — | — |
| 5 | 32 | 32 | 8+ | 64+ | — | — | — | — |
| 6 | 1* | 8 | 1* | 32* | 64* | 4* | 8* | 4* |
| 11 | 32 | 32 | >64 | >64 | >64 | — | — | — |

Legend:
w.s. = with 30% serum added
n.s. = no serum added
* = 90% inhibition of growth
+ = 50% inhibition of growth Anti-mycotic action of the compounds according to the invention in animal experiments.

a. Action on *Quinckeanum trichopytosis* in white mice, on oral administration.

With doses of 2 × 100 mg/kg administered orally once daily up to the eighth day of the infection, it was possible to suppress the development of the Quinckeanum infection in mice. After administration of the compounds according to the invention, 0 to 2 out of 20 treated mice, in contrast to 19 out of 20 animals of the untreated control, showed scutula, which are to be regarded as a typical signa of infection of *Quinckeanum trichophytosis*, ten day after the infection.

b. Candidosis of mice.

Mice of type SPF—$CF_1$ were intravenously infected with 1 to 2 × $10^6$ *Candida* cells which were suspended in physiological sodium chloride solution.

One hour before and seven hours after infection, the animals were treated orally with 50, 75, 100 and 150 mg of the compounds according to the invention/kg of body weight. Untreated control animals died of the infection, 3 to 6 days after infection.

The experimental results are summarised in Table B.

Table B

| | Action in Candidosis of mice |
|---|---|
| Compound from Example No. | Action in the case of *Candida albicans* |
| 2 | + |
| 12 | + |

Table B-continued

| Compound from Example No. | Action in Candidosis of mice Action in the case of *Candida albicans* |
|---|---|
| 7 | ++ |

Legend:
+ = 50% survivals on 6th day after infection
++ = 60 to 80% survivals on 6th day after infection.

The following Examples illustrate the invention.

EXAMPLE 1

Process Variant (a):

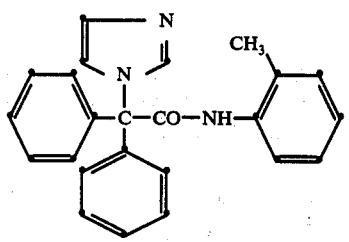

134.5 g (0.4 mol) of chlorodiphenylacetic acid o-methylanilide are dissolved in 500 ml of anhydrous acetonitrile and 40.4 g (0.4 mol) of triethylamine are added. 27.2 g (0.4 mol) of imidazole are added dropwise thereto at room temperature, and the reaction mixture is heated to the boil for 16 hours. After cooling, the solvent is distilled off in vacuo until one-quarter remains and the resulting residue is digested with ice water. The insoluble product is filtered off, dried and briefly heated to the boil with acetone. The residue is filtered off and dried.

47.5 g (32.4% of theory) of ω,ω-diphenyl-ω-imidazolyl-(1)-acetic acid o-methylanilide, of melting point 141° to 143° C, are obtained.

Process Variant (b):

52.8 g (0.2 mol) of chlorodiphenylacetic acid chloride are dissolved in 300 ml of anhydrous acetonitrile and 55 g (0.8 mol) of imidazole are added. After heating for 16 hours under reflux, the mixture is cooled, 21.5 g (0.2 mol) of o-methylaniline are added and the mixture is again heated to the boil under reflux for 16 hours. Thereafter it is worked up as indicated above.

26.1 g (34.5% of theory) of ω,ω-diphenyl-ω-imidazolyl-(1)-acetic acid o-methylanilide of melting point 141 to 143° C are obtained.

EXAMPLE 2

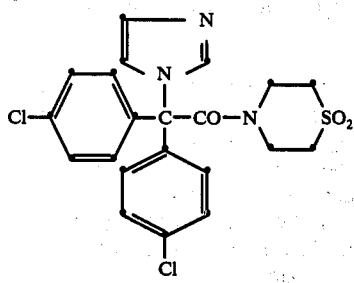

42.9 g (0.1 mol) of [ω,ω-di-(4-chlorophenyl)-ω-chloromethylcarbonyl-(4)]-1,4-thiazine dioxide are dissolved in 150 ml of anhydrous acetonitrile and 13.6 g (0.2 mol) of imidazole are added dropwise thereto, at the boil. Thereafter the mixture is heated to the boil for 16 hours and cooled, and the solvent is distilled from the reaction mixture in vacuo, except for a small residual amount. The semi-crystalline residue is stirred with ice water. The solid product thereby produced is filtered off and recrystallized from acetonitrile.

30.6 g (66% of theory) of [ω,ω-di(4-chlorophenyl)-ω-imidazolyl-(1)-methylcarbonyl-(4)]-1,4-thiazine dioxide of melting point 159° to 163° C are obtained.

Alternatively, 0.2 mol of ω,ω-di-(4-chlorophenyl)-ω-chloroacetic acid chloride are dissolved in 300 ml of anhydrous acetonitrile and 0.8 mol of imidazole are added. After heating for 16 hours under reflux, the mixture is cooled, 0.2 mol of 1,4 triazine-1,1-dioxide are added and the mixture is again heated to the boil under reflux for 16 hours. Thereafter it is worked up as indicated above.

The compounds in Table 1 below are produced in a manner analogous to that described in Examples 1 and 2 from the reactants set forth in Tables 2 and 3.

Table 1

| Ex. No. | $X^1$ | $X^2$ | $X^3$ | $X^4$ | $R^1$ | $R^2$ | Melting point °C |
|---|---|---|---|---|---|---|---|
| 3 | H | H | H | H | ⌬-Cl | H | 206–208 |
| 4 | H | H | H | H | ⌬-CF₃ | H | 219–220 |
| 5 | H | H | H | H | CF₃-⌬-Cl | H | 178–179 |
| 6 | H | H | H | H | Cl-⌬-Cl | H | 115 |
| 7 | H | H | H | H | ⌬-H | H | 166–168 |

| Ex. No. | $X^1$ | $X^2$ | $X^3$ | $X^4$ | $RT^1$ and $R^2$ | Melting point °C |
|---|---|---|---|---|---|---|
| 8 | H | H | H | H | ⌬SO₂ | 272–275 |

Table 1-continued

| | X¹ | X² | X³ | X⁴ | NR¹R² | m.p. |
|---|---|---|---|---|---|---|
| 9 | H | H | H | H | (tetrahydrothiazine-SO₂ with CH₃) | 266–268 |
| 10 | H | H | H | H | (tetrahydrothiazine-SO₂ with C₂H₅) | 256–258 |
| 11 | 4-Cl | H | 4-Cl | H | (tetrahydrothiazine-SO₂ with CH₂-phenyl) | 103–104 |
| 12 | H | H | H | H | piperazine-N—COOC₂H₅ | 156–158 |
| 13 | H | H | H | H | piperazine-N-(2-chlorophenyl) | 260–262 |
| 14 | H | H | H | H | piperazine-N—CO—N(C₂H₅)₂ | 166–168 |
| 15 | H | H | H | H | piperazine-N—CH(phenyl)₂ | 220–222 |

Table 2

The compounds of Examples 3 through 15 are produced according to Process Variant (a) by reacting imidazole with:

| Example No. | |
|---|---|
| 3 | w,w-diphenyl-w-chloro-acetic acid p-chloroanilide |
| 4 | w,w-diphenyl-w-chloro-acetic acid m-trifluoromethyl-anilide |
| 5 | w,w-diphenyl-w-chloro-acetic acid 2-methyl-4-chloro anilide |
| 6 | w,w-diphenyl-w-chloro-acetic acid 2,4-dichloro-anilide |
| 7 | — |
| 8 | [w,w-diphenyl-w-chloro-methylcarbonyl]-1,4-thiazine dioxide |
| 9 | 3-methyl-4-[w,w-diphenyl-w-chloro-methylcarbonyl]-1,4-thiazine dioxide |
| 10 | 3-ethyl-4-[w,w-diphenyl-w-chloro-methylcarbonyl]-1,4-thiazine dioxide |
| 11 | 3-phenyl-4-[w,w-di-(4-chlorophenyl)-w-chloromethyl-carbonyl]-1,4-thiazine dioxide |
| 12 | 1-Ethoxycarbonyl-4-[w,w-diphenyl-w-chloromethyl-carbonyl]-piperazine |
| 13 | 1-O-chlorophenyl-4-[w,w-diphenyl-w-chloro-methyl-carbonyl]-piperazine |
| 14 | 1-diethylaminocarbonyl-4-[w,w-diphenyl-w-chloro-methylcarbonyl]-piperazine |
| 15 | 1-diphenylmethyl-4-[w,w-di-(4-chloro-phenyl)-w-chloro-methylcarbonyl]-piperazine |

Table 3

The compounds of Examples 3 through 15 are produced according to Process Variant (b) by reacting imidazole with:

| Example No. | |
|---|---|
| 2 | w,w-di-(p-chlorophenyl)-w-chlor-acetic acid chloride |
| 4 | w,w-diphenyl-w-chloro-acetic acid chloride |
| 5 | w,w-diphenyl-w-chloro-acetic acid chloride |
| 6 | w,w-diphenyl-w-chloro-acetic acid chloride |
| 7 | w,w-dipahenyl-w-chloro-acetic acid chloride |
| 8 | — |
| 9 | — |
| 10 | — |
| 11 | w,w-di-(4-chlorophenyl)-w-chloro-acetic acid chloride |
| 12 | w,w-diphenyl-w-chloro-acetic acid chloride |
| 13 | w,w-diphenyl-w-chloro-acetic acid chloride |
| 14 | — |
| 15 | — | to produce an imidazolide which is thereafter transaminated by reaction with an amine.

What is claimed is:

1. A pharmaceutical composition for treating mycotic infections in humans and animals which comprises an antimycotically effective amount of an imidazolylacetic acid amide of the formula:

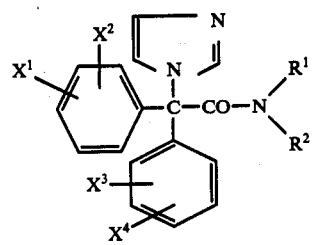

or a pharmaceutically acceptable nontoxic salt thereof wherein $R^1$ and $R^2$, together with the nitrogen atom to which they are attached form a saturated 6-membered heterocyclic ring containing a —NY— moiety wherein Y is alkoxycarbonyl of 2 to 4 carbon atoms, dialkylaminocarbonyl of 1 to 4 carbon atoms in each alkyl moiety, phenyl or diphenylmethyl, and $X^1$, $X^2$, $X^3$ and $X^4$ are the same or different and are each hydrogen or halogen;

in combination with a pharmaceutically acceptable, nontoxic, inert carrier.

2. A composition according to claim 1 wherein $R^1$ and $R^2$, together with the nitrogen atom to which they are attached, form a saturated 6-membered heterocyclic ring containing a —NY— moiety wherein Y is phenyl, diphenylmethyl, methoxycarbonyl, ethoxycarbonyl, dimethylaminocarbonyl or diethylaminocarbonyl, and either
$X^1$, $X^2$, $X^3$ and $X^4$ are each hydrogen, or
$X^1$ and $X^3$ are each halogen and
$X^2$ and $X^4$ are each hydrogen.

3. A composition according to claim 2 wherein $R^1$ and $R^2$, together with the nitrogen atom to which they are attached, form a saturated 6-membered heterocyclic ring containing a —NY— moiety wherein Y is phenyl, diphenylmethyl, methoxycarbonyl, ethoxycarbonyl, dimethylaminocarbonyl or diethylaminocarbonyl, and either
$X^1$, $X^2$, $X^3$ and $X^4$ are each hydrogen, or
$X^1$ and $X^3$ are each chlorine and
$X^2$ and $X^4$ are each hydrogen.

4. A composition according to claim 1 wherein $R^1$ and $R^2$, together with the nitrogen atom to which they are attached, form a 6-membered heterocycle selected from the group consisting of:

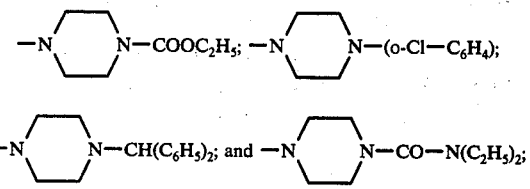

and either
$X^1$, $X^2$, $X^3$ and $X^4$ are each hydrogen, or
$X^1$ and $X^3$ are chlorine and
$X^2$ and $X^4$ are hydrogen.

5. A composition according to claim 1 wherein $R^1$ and $R^2$, together with the nitrogen atom to which they are attached, form a saturated 6-membered heterocyclic ring of the formula:

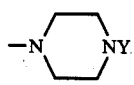

wherein
Y is $COOC_2H_5$, chlorophenyl, $CO-N(C_2H_5)_2$, or diphenylmethyl; and either
$X^1$, $X^2$, $X^3$ and $X^4$ are each hydrogen or
$X^1$ and $X^3$ are chlorine and
$X^2$ and $X^4$ are hydrogen.

6. A composition according to claim 1 wherein the imidazolylacetic acid amide is in the form of a pharmaceutically acceptable nontoxic salt selected from the group consisting of the hydrochloride, the hydrobromide, the phosphate, nitrate, acetate, maleate, succinate, fumarate, tartrate, citrate, salicylate, sorbate, lactate, and 1,5-naphthalenedisulphonate.

7. The composition according to claim 6 wherein the salt is the hydrochloride.

8. The composition according to claim 1 wherein $R^1$ and $R^2$, together with the nitrogen atom to which they are attached, form a saturated 6-membered heterocyclic moiety of the formula:

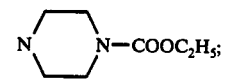

and $X^1$, $X^2$, $X^3$ and $X^4$ are each hydrogen.

9. The composition according to claim 1 wherein $R^1$ and $R^2$, together with the nitrogen atom to which they are attached, form a saturated 6-membered heterocyclic moiety of the formula:

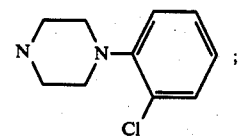

and
$X^1$, $X^2$, $X^3$ and $X^4$ are each hydrogen.

10. The composition according to claim 1 wherein $R^1$ and $R^2$, together with the nitrogen atom to which they are attached, form a saturated 6-membered heterocyclic moiety of the formula:

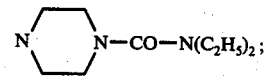

and
$X^1$, $X^2$, $X^3$ and $X^4$ are each hydrogen.

11. The composition according to claim 1 wherein $R^1$ and $R^2$, together with the nitrogen atom to which they are attached, form a saturated 6-membered heterocylic moiety of the formula:

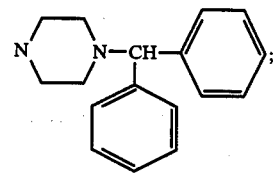

and $X^1$, $X^2$, $X^3$ and $X^4$ are each hydrogen.

12. A composition according to claim 1 in oral administration form.

13. A composition according to claim 1 in topical application form.

14. A method of treating mycoses in humans and animals which comprises administering to a human or animal in need thereof an antimycotically effective amount of an imidazolylacetic acid amide of the formula

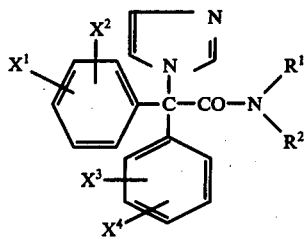

or a pharmaceutically acceptable nontoxic salt thereof wherein

R¹ and R², together with the nitrogen atom to which they are attached form a saturated 6-membered heterocyclic ring containing a -NY-moiety wherein Y is alkoxycarbonyl of 2 to 4 carbon atoms, dialkylaminocarbonyl of 1 to 4 carbon atoms in each alkyl moiety, phenyl or diphenylmethyl, and $X^1$, $X^2$, $X^3$ and $X^4$ are the same or different and are each hydrogen or halogen.

15. A method according to claim 14 wherein

R¹ and R², together with the nitrogen atom to which they are attached, form a saturated 6-membered heterocyclic ring containing a —NY— moiety wherein Y is phenyl, diphenylmethyl, methoxycarbonyl, ethoxycarbonyl, dimethylaminocarbonyl, and either $X^1$, $X^2$, $X^3$ and $X^4$ are each hydrogen, or
$X^1$ and $X^3$ are each halogen and
$X^2$ and $X^4$ are each hydrogen.

16. A method according to claim 14 wherein

R¹ and R², together with the nitrogen atom to which they are attached, form a saturated 6-membered heterocyclic ring containing a —NY— moiety wherein Y is phenyl, diphenylmethyl, methoxycarbonyl, ethoxycarbonyl, dimethylaminocarbonyl or diethylaminocarbonyl, and either $X^1$, $X^2$, $X^3$ and $X^4$ are each hydrogen, or
$X^1$ and $X^3$ are each chlorine and
$X^2$ and $X^4$ are each hydrogen.

17. A method according to claim 14 wherein

R¹ and R², together with the nitrogen atom to which they are attached, form a 6-membered heterocycle selected from the group consisting of:

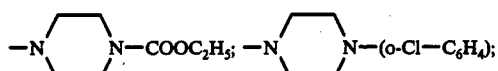
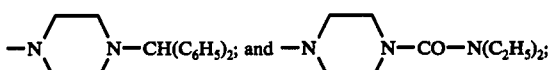

and either $X^1$, $X^2$, $X^3$ and $X^4$ are each hydrogen, or
$X^1$ and $X^3$ are chlorine and
$X^2$ and $X^4$ are hydrogen.

18. A method according to claim 14 wherein

R¹ and R², together with the nitrogen atom to which they are attached, form a saturated 6-membered heterocyclic ring of the formula:

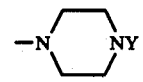

wherein

Y is $COOC_2H_5$, chlorophenyl, $CO-N(C_2H_5)_2$, or diphenylmethyl; and either $X^1$, $X^2$, $X^3$ and $X^4$ are each hydrogen, or
$X^1$ and $X^3$ are each chlorine and
$X^2$ and $X^4$ are each hydrogen.
$X^2$ and $X^4$ are hydrogen.

19. A method according to claim 14 wherein the imidazolylacetic acid amide is in the form of a pharmaceutically acceptable nontoxic salt selected from the group consisting of the hydrochloride, the hydrobromide, the phosphate, nitrate, acetate, maleate, succinate, fumarate, tartrate, citrate, salicylate, sorbate, lactate, and 1,5-naphthalenedisulphonate.

20. A method according to claim 19 wherein the salt is the hydrochloride.

21. A method according to claim 14 wherein

R¹ and R², together with the nitrogen atom to which they are attached, form a saturated 6-membered heterocyclic moiety of the formula:

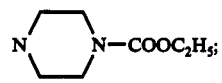

and
$X^1$, $X^2$, $X^3$ and $X^4$ are each hydrogen.

22. A method according to claim 14 wherein

R¹ and R², together with the nitrogen atom to which they are attached, form a saturated 6-membered heterocyclic moiety of the formula:

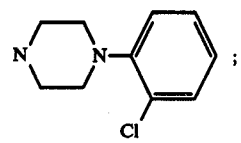

and
$X^1$, $X^2$, $X^3$ and $X^4$ are each hydrogen.

23. A method according to claim 14 wherein

R¹ and R², together with the nitrogen atom to which they are attached, form a saturated 6-membered heterocyclic moiety of the formula:

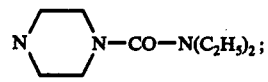

and
$X^1$, $X^2$, $X^3$ and $X^4$ are each hydrogen.

24. A method according to claim 14 wherein

R¹ and R², together with the nitrogen atom to which they are attached, form a saturated 6-membered heterocyclic moiety of the formula

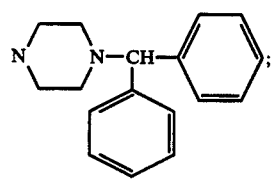

and
$X^1$, $X^2$, $X^3$ and $X^4$ are each hydrogen.

25. A method according to claim 14 wherein the administration is oral.

26. A method according to claim 14 wherein the administration is by topical application.

* * * * *

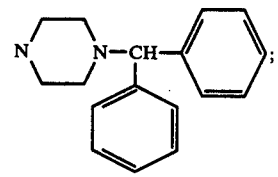

and
$X^1$, $X^2$, $X^3$ and $X^4$ are each hydrogen.

25. A method according to claim 14 wherein the administration is oral.

26. A method according to claim 14 wherein the administration is by topical application.

* * * * *